United States Patent
Oh

(10) Patent No.: US 7,097,454 B1
(45) Date of Patent: Aug. 29, 2006

(54) ENDODONTIC GUTTA-PERCHA POINT WITH WORKING LENGTH MARKS

(76) Inventor: Suk-song Oh, 426-11 Shinsu-dong, Mapo-gu, Seoul (KR)

(*) Notice: Subject to any disclaimer, the term of this patent is extended or adjusted under 35 U.S.C. 154(b) by 71 days.

(21) Appl. No.: 09/294,073

(22) Filed: Apr. 19, 1999

(30) Foreign Application Priority Data

Sep. 12, 1998 (KR) ................................ 1998-37719

(51) Int. Cl.
*A61C 5/02* (2006.01)
(52) U.S. Cl. ........................................ 433/224; 433/81
(58) Field of Classification Search .................. 433/81, 433/102, 224, 75
See application file for complete search history.

(56) References Cited

U.S. PATENT DOCUMENTS

| | | | | |
|---|---|---|---|---|
| 1,757,595 A | * | 5/1930 | Siegel | 433/224 |
| 3,772,791 A | * | 11/1973 | Malmin | 433/75 |
| 3,855,702 A | * | 12/1974 | Malmin | 433/165 |
| 3,935,640 A | * | 2/1976 | Cohen | 433/75 |
| 5,118,297 A | | 6/1992 | Johnson | 433/224 |
| 5,149,268 A | | 9/1992 | Johnson | 433/224 |
| 5,833,457 A | * | 11/1998 | Johnson | 433/224 |
| 5,833,458 A | * | 11/1998 | Harrisson, III | 433/224 |
| 6,264,471 B1 | * | 7/2001 | Martin | 433/224 |

* cited by examiner

*Primary Examiner*—John J Wilson
(74) *Attorney, Agent, or Firm*—Seth Natter; Natter & Natter

(57) ABSTRACT

A gutta-percha point, used as a root canal plugging material in an endodontic treatment, is disclosed. The gutta-percha point has a plurality of engraved or embossed marks as working length marks on its upper portion. Each of the engraved or embossed marks is preferably painted with a distinguishable color along a circumferential surface. The above marks are formed on the point within a marking range while being spaced out at intervals of 1 mm and 2 mm. The marking range starts at a position, spaced apart from the apex of the point by 18 mm, and ends at a position spaced apart from the apex by 24 mm. The gutta-percha point thus allows an endodontist to be free from a repeated marking of working lengths on such points during an endodontic treatment, thus allowing the endodontic treatment to be accomplished within a desired short period of time. Due to the working length marks, the gutta-percha point is precisely inserted into an access cavity of a decayed tooth by a desired depth, thus being free from forming a dead space in the root canal or piercing the apical tissue.

7 Claims, 4 Drawing Sheets

ENDODONTIC GUTTA-PERCHA POINT WITH WORKING LENGTH MARKS

BACKGROUND OF THE INVENTION

1. Field of the Invention

The present invention relates, in general, to gutta-percha points used as plugging materials for root canals in endodontic treatments and, more particularly, to an endodontic gutta-percha point having working length marks at its upper portion.

2. Description of the Prior Art

As well known to those skilled in the art, gutta percha is a material, which is extracted from palaguium or payena generic plants of sapotaceae, the native plants of the Malay Archipelago. The gutta percha has a semisolid phase at an ordinary temperature, but is changed in the phase when it is pressurized or heated. When the gutta percha is heated to a temperature higher than 60° C., it becomes a plastic.

Gutta-percha points, used as plugging materials for a root canal in an endodontic treatment, may be different in their concentrations of components according to manufacturers of the points. However, most of gutta-percha points typically consist of 66% of zinc oxide, 20% of gutta percha, 11% of heavy metal sulphate (a radio-opacity material), and 3% of wax or resin used as a plasticizer.

Such gutta-percha points are problematic in that it is somewhat difficult to insert the points into narrow root canals and it is necessary to use a sealer in order to seal the root canals after inserting the points into the canals.

Another problem, experienced in typical gutta-percha points, resides in that they may be easily broken when a period of time has passed after manufacture.

However, the gutta-percha points preferably meet most of the needs typically desired from plugging materials for root canals in endodontic treatments.

Since the gutta-percha points are plastic materials, they are preferably accepted by an access cavity for the root canal and are easy to treat.

In addition, it is somewhat easy to remove the gutta-percha points from root canals in the case of a root canal retreatment or a dentodic operation. The gutta-percha points also have a low toxic effect to an apical tissue.

Gutta-percha points, which are marketed now, are generally classified into two types: standardized points and conventional points.

The standardized gutta-percha points are sized and tapered in the same scale as that of typical endodontic instruments, thus being more generally used by endodontists.

Such gutta percha has been used as a material of endodontic plugging points for 100 years or more. However, there has not been proposed another material which is more acceptable or preferable than the gutta percha as a material of the endodontic plugging points. Therefore, the gutta-percha points are widely and preferably used as root canal plugging points in endodontic treatments.

FIGS. 3a to 3g schematically show an endodontic treatment process of treating a decayed root canal using the conventional gutta-percha points.

A root canal is typically infected as follows. As shown in FIG. 3a, a tooth "T" is initially decayed at the enamel 31. The decaying of the tooth is, thereafter, propagated to the dentine 32, the pulp cavity 33 and the root canal 34 in order. The pulp tissue in the tooth T is also infected in accordance with the propagation of decaying. When the pulp tissue is decayed, a patient feels pain.

A root canal treatment for such a decayed tooth T is carried out as follows. In order to treat the decayed tooth T, it is primarily necessary to prepare an access cavity 35 in the tooth T as shown in FIG. 3b.

In order to form such an access cavity 35, the decayed portions of both the enamel 31 and the dentine 32 are removed from the tooth T using an endodontic instrument, such as a file or a reamer. In such a case, the decayed pulp tissue has to be also removed. The access cavity 35 is enlarged by smoothing the interior surface of the cavity 35 using the endodontic instrument. The enlarged and smoothed cavity 35 is finally sterilized and dried using paper points.

After the access cavity 35 is primarily formed in the tooth T, it is necessary to measure a working length WL from the top of the tooth T to the apical foramen 36 as shown in FIG. 3c.

In such a case, the measurement of the working length WL in the decayed tooth T is for limiting the access area for endodontic instruments, medicines and plugging materials so as to prevent the apical tissue from any damage during both an access cavity preparation process and a root canal plugging process.

Of course, there may be different working lengths WL in accordance with patients, teeth T, and positions of apical foramens 36. However, such working lengths WL typically range from about 18 mm to about 24 mm.

The measurement of the working length WL is performed using a file 37 with a silicon rubber stopper 38. That is, in order to measure the working length WL, the file 37 is primarily inserted into the access cavity 35 until the apex of the file 37 reaches a position around the apical foramen 36 without piercing the apical tissue or giving pain to the tissue. Thereafter, an X-ray inspection is carried out so as to determined whether the apex of the file 37 is appropriately accepted by the apical foramen 36 or not. When the X-ray inspection shows that the apex of the file 37 is appropriately accepted by the apical foramen 36, the stopper 38 is adjusted along the file 37 until the stopper 38 meets the top of the tooth T. In such a case, the length from the apex of the file 37 to the stopper 38 is the working length WL.

The working length WL on the file 37 is measured using an endodontic ruler which shows the length WL as a numerical value. Thereafter, gutta-percha points, including master and accessory points, are measured using the endodontic ruler so as to determine a length, which is equal to the calculated working length WL, on each point. In such a case, the length measurement of the gutta-percha points is started from the sharpened apex of each point. After measuring a working length WL of each gutta-percha point using the endodontic ruler, the end of the length WL opposite to the apex is marked on each point prior to starting a root canal plugging process using the points. The root canal plugging process is shown in FIG. 3d.

In the root canal plugging process, a sealer is primarily applied to the access cavity 35. Thereafter, the master point of the gutta-percha points is inserted into the tooth T until the mark of the working length WL on the master point is aligned with the top of the tooth T. The insertion of the master point is followed by an insertion of accessory points. That is, after the insertion of the master point, a plurality of accessory points of the gutta-percha points are inserted into the access cavity 35 at positions around the master point using a spreader. The insertion of the accessory point is also carried out through a lateral condensation method. In the root canal plugging process, it is also necessary to prevent any gap from being left in the access cavity 35 filled with the points.

In the above plugging process, it is preferable to make the apex of each gutta-percha point precisely aligned with the apical foramen 36 of the access cavity 35.

When the apex of each gutta-percha point fails to reach the apical foramen 36, a dead space is formed at an area between the apex of the point and the apical foramen 36. Such a dead space may allow a propagation of bacteria at that space and this forces the patient to suffer from the root canal retreatment. On the other hand, when the sharpened apex of each gutta-percha point exceeds the apical foramen 36 and pierces into the apical tissue, the apex of the point pressurizes the apical tissue and gives the patient pain.

Therefore, it is necessary to insert the gutta-percha points, particularly, the master point, into the access cavity 35 with the apex of each point being appropriately accepted by the apical foramen 36. In order to accomplish the above object, it is very important to precisely mark the working length WL on each point, particularly, the master point, and to precisely insert the points into the access cavity 35 by the working length WL.

After inserting the gutta-percha points into the access cavity 35, the upper portions of the points are removed using a plugger with the lower portions of the points being left in the enlarged root canal as shown in FIG. 3e.

FIG. 3f shows an amalgam 39 filling in the upper portion of the access cavity 35 with the gutta-percha points plugging the enlarged root canal.

As shown in FIG. 3g, a gold crown 40 is, thereafter, exteriorly set on the top portion of the tooth T filled with both the gutta-percha points and the amalgam 39 in the access cavity 35. An endodontic treatment process is thus accomplished.

However, the above-mentioned process gives inconvenience to both endodontists and patients due to a structural defect of the typical gutta-percha points. That is, in the above process, it is necessary for an endodontist to measure a working length WL using a file 37. The working length WL on the file 37 is measured using an endodontic ruler which shows the length WL as a numerical value. Thereafter, gutta-percha points, including master and accessory points, are measured using the endodontic ruler so as to determine a length, which is equal to the calculated working length WL, on each point prior to marking the upper end of the length WL opposite to the apex of each point. However, typical gutta-percha points 20 are free from any working length marks on its surface as shown in FIG. 1. Therefore, it is necessary for endodontists to mark the working lengths WL on the gutta-percha points 20 during root canal treatments. In order to mark the working lengths WL on the points 20, each point 20 may be bent at a position corresponding to the upper end of the length WL, thus forming a bent portion 21 on the point 20 as shown in FIG. 2a. Alternatively, the working length WL may be marked on each point 20 by pressing the point 20 using an appropriate marking instrument, such as a pincette, at a position corresponding to the upper end of the length WL, thus forming a pressed mark 22 on the point 20. Of course, there may be other methods of forming the mark of the working length WL on each of the gutta-percha points 20.

Therefore, the typical gutta-percha points 20 are problematic in that they force an endodontist to repeatedly and manually measure a working length-WL and to form the bent portions 21 or the pressed marks 22 on the points 20 during a root canal treatment. Such gutta-percha points 20 thus consume time and this is inconvenient to both the endodontists and patients since it is necessary to precisely perform a root canal treatment within a somewhat short period of time with the mouth of a patient being continuously and fully opened.

Furthermore, there may occur an undesired error while measuring a working length WL with an endodontic ruler or forming a bent portion 21 or a pressed mark 22 on each point 20 so as to mark the working length WL on each point 20 during a root canal treatment. Such an error makes the apexes of the points 20 fail to be precisely aligned with an apical foramen 36. This regrettably results in an operational error during a root canal treatment.

SUMMARY OF THE INVENTION

Accordingly, the present invention has been made keeping in mind the above problems occurring in the prior art, and an object of the present invention is to provide an endodontic gutta-percha point having working length marks at its upper portion.

In order to accomplish the above object, the present invention provides an endodontic gutta-percha point, which has a plurality of engraved or embossed marks as working length marks on its upper portion, thus allowing endodontists to be free from a repeated marking of working lengths on the gutta-percha points while plugging an enlarged root canal with the points during an endodontic treatment. This allows the root canal plugging process to be accomplished within a desired short period of time. The working length marks of the gutta-percha points also allow an endodontist to precisely insert the points into an access cavity of a decayed tooth by a desired depth without failure.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 4:
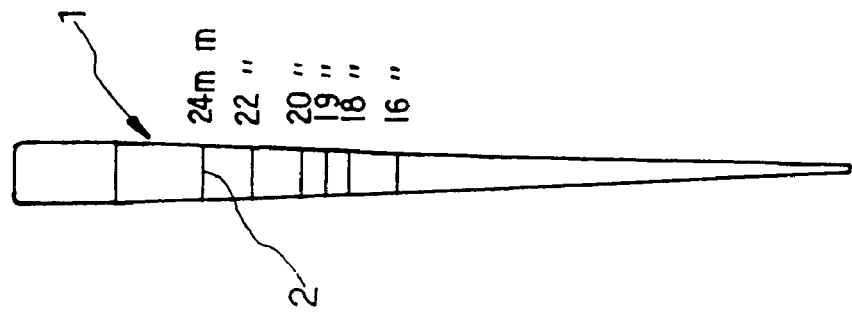
FIG. 4 is a front view of a gutta-percha point with a plurality of working length marks in accordance with the primary embodiment of the present invention.

FIG. 4 is a front view of a gutta-percha point with a plurality of working length marks in accordance with the primary embodiment of this invention. As shown in the drawing, the gutta-percha point 1 according to the invention has a plurality of working length marks 2 along its upper portion, with the marks 2 being spaced apart from each other. In the primary embodiment, the marks 2 are formed on the point 1 through an embossing process.

The working length marks 2 are formed on the upper portion of the point 1 within a marking range, the range starting at a position spaced apart from the sharpened apex of the point 1 by 18 mm and ending at a position spaced apart from said apex by 24 mm. The marks 2 are also spaced out at different intervals of 1 mm and 2 mm.

In order to allow the marks 2 to be somewhat prominently distinguished by users or endodontists, it is preferable to paint the circumferential surface of each embossed mark 2 with a distinguishable color.

Figure 5:
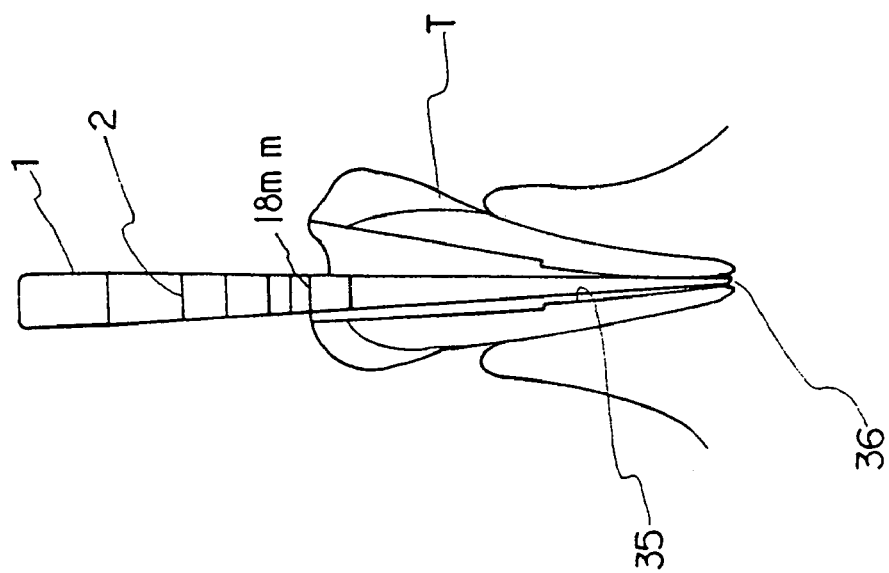
FIG. 5 is a view showing the gutta-percha point of FIG. 4 which is appropriately inserted into an access cavity of a decayed tooth during an endodontic treatment process.

The above gutta-percha point 1 is used as follows. FIG. 5 shows the point 1 appropriately inserted into an access cavity of a decayed tooth during an endodontic treatment process. When the point 1 is used for plugging an enlarged root canal of a decayed tooth T having a working length WL of 18 mm, the point 1 is inserted into an access cavity 35 of the tooth T until an 18 mm mark 2, corresponding to the 18 mm working length, is precisely aligned with the top of the tooth T. When the 18 mm mark 2 is precisely aligned with the top of the tooth T, the apex of the point 1 is precisely aligned with the apical foramen 36, thus being free from forming a dead space in the root canal or passing through the apical foramen 36 so as to pierce the apical tissue.

Figure 2B:
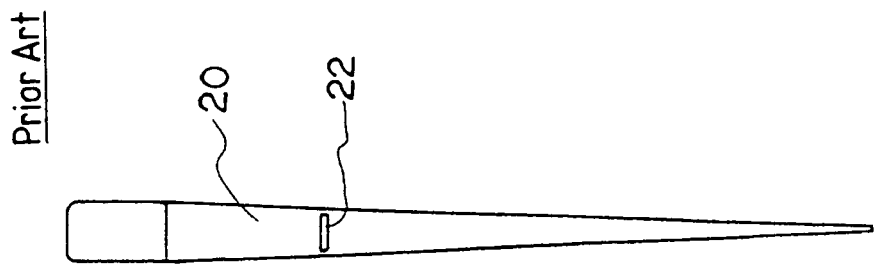
FIGS. 2a and 2b are views, respectively showing typical methods of marking a working length on a conventional gutta-percha point.
Figure 2A:
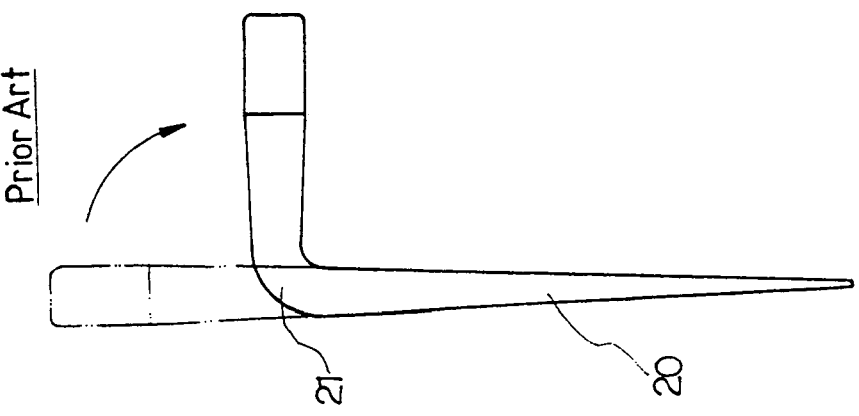
Figure 1:
FIG. 1 is a front view of a conventional gutta-percha point used as a root canal plugging material in an endodontic treatment.
Figure 3A:
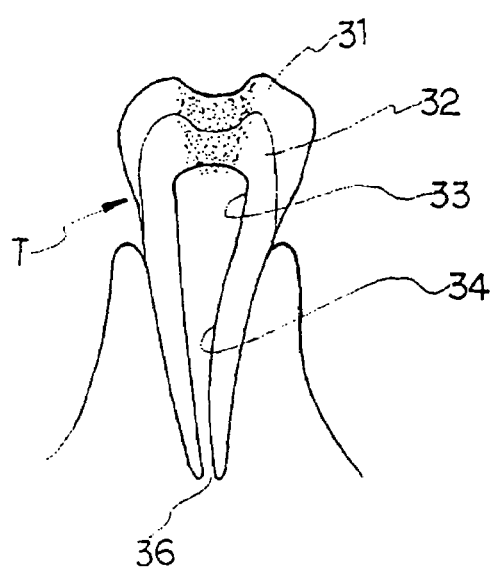
FIGS. 3a to 3g are views, schematically showing an endodontic treatment process of treating a decayed root canal using such conventional gutta-percha points.
Figure 3B:
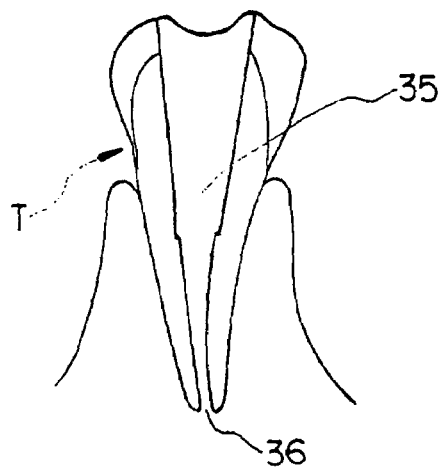
Figure 3C:
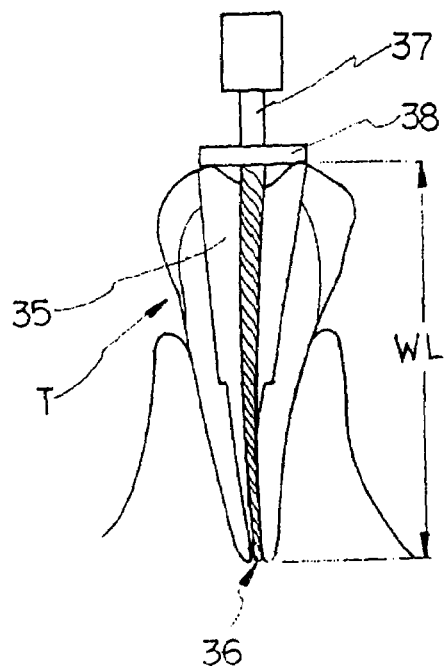
Figure 3D:
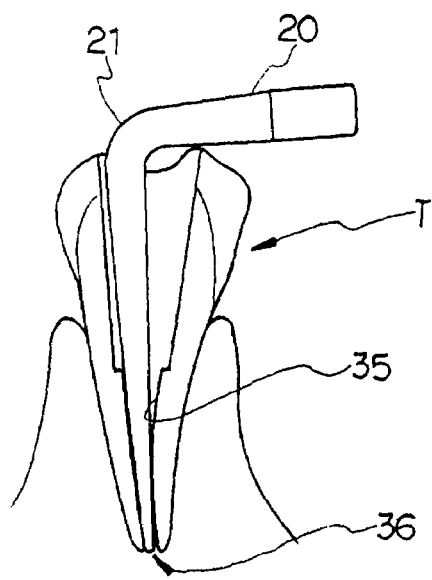
Figure 3E:
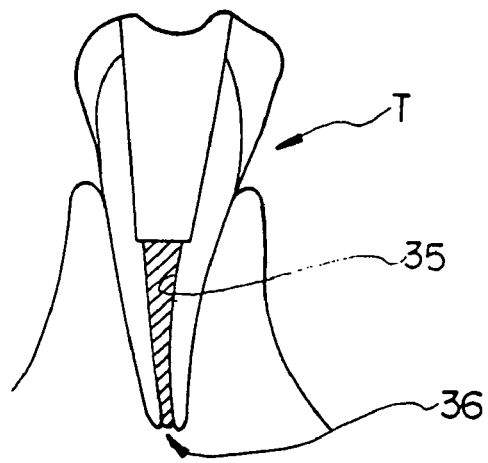
Figure 3F:
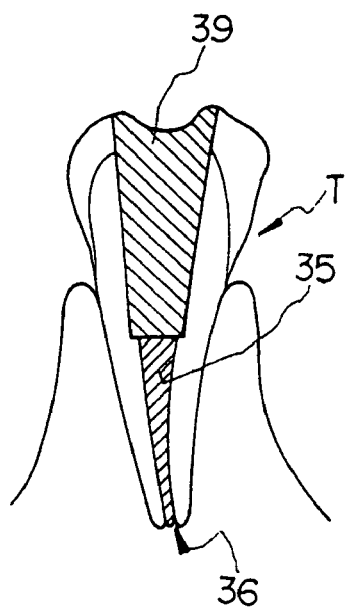
Figure 3G:
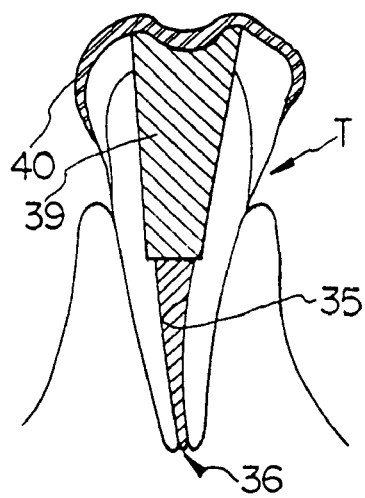
Figure 6:
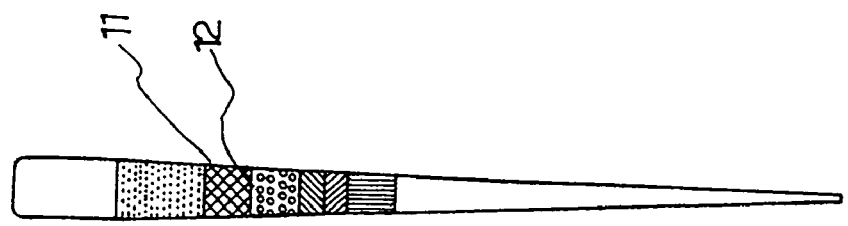
FIG. 6 is a front view of a gutta-percha point with a plurality of working length marks in accordance with the second embodiment of the present invention.

FIG. 6 shows a gutta-percha point with a plurality of working length marks in accordance with the second embodiment of this invention. In the second embodiment, the gutta-percha point 11 has a plurality of working length marks 12 along its upper portion in the same manner as that described for the primary embodiment. However, the marks 12 of the second embodiment are formed on the point 11 through an engraving process different from the primary embodiment.

In the same manner as that described for the primary embodiment, the working length marks 12 are formed on the upper portion of the point 11 within a marking range. The marking range starts at a position spaced apart from the sharpened apex of the point 11 by 18 mm and ends at a position spaced apart from said apex by 24 mm. The marks 12 are also spaced out at different intervals of 1 mm and 2 mm.

In order to allow the marks 12 to be somewhat prominently distinguished by users or endodontists, the circumferential surface of each embossed mark 2 is preferably painted with a distinguishable color.

The above gutta-percha point 11 is used as follows. When the point 11 is used for plugging an enlarged root canal of a decayed tooth T having a working length WL of 18 mm, the point 11 is inserted into an access cavity 35 of the tooth T until an 18 mm mark 12, corresponding to the 18 mm working length, is precisely aligned with the top of the tooth T. When the 18 mm mark 12 is precisely aligned with the top of the tooth T, the apex of the point 1 is precisely aligned with the apical foramen 36, thus being free from forming a dead space in the root canal or passing through the apical foramen 36 so as to pierce the apical tissue.

As described above, the present invention provides a gutta-percha point used as a root canal plugging material in an endodontic treatment. The gutta-percha point of this invention has a plurality of engraved or embossed marks as working length marks on its upper portion. The point thus allows endodontists to be free from a repeated marking of working lengths on the gutta-percha points while plugging an enlarged root canal with the points during an endodontic treatment. This allows the root canal plugging process to be accomplished within a desired short period of time. The working length marks of the gutta-percha points also allow an endodontist to precisely insert the points into an access cavity of a decayed tooth by a desired depth without failure. Therefore, the gutta-percha point is free from forming a dead space in the root canal or passing through an apical foramen so as to pierce an apical tissue. The gutta-percha points of this invention thus allow endodontists to appropriately accomplish desired root canal treatments within a short period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A gutta-percha point used as a root canal plugging material in an endodontic treatment, said plugging point including a plurality of integral working length marks along an upper portion of said point, said marks spaced apart from each other.

2. The gutta-percha point according to claim 1 wherein said working length marks include distinguishable colors.

3. The gutta-percha point according to claim 2 wherein said working length marks are along a circumferential surface of said point.

4. The gutta-percha point according to claim 1, wherein said working length marks are painted.

5. The gutta-percha point according to claim 1 wherein said working length marks start at a position starting from an apex of said point by 18 mm and ending at a position spaced apart from said apex by 22 mm.

6. The gutta-percha point according to claim 1, wherein said working length marks are embossed.

7. The gutta-percha point according to claim 1, wherein said working length marks are engraved.

* * * * *